(12) United States Patent
McClellan, III et al.

(10) Patent No.: US 8,652,143 B2
(45) Date of Patent: Feb. 18, 2014

(54) INSERTER DEVICE USED FOR ORTHOPEDIC SURGERY

(75) Inventors: John W. McClellan, III, Omaha, NE (US); YoungHoon Oh, Montville, NJ (US); Mahmoud F. Abdelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 1424 days.

(21) Appl. No.: 11/841,039

(22) Filed: Aug. 20, 2007

(65) Prior Publication Data

US 2009/0054901 A1 Feb. 26, 2009

(51) Int. Cl.
*A61B 17/58* (2006.01)

(52) U.S. Cl.
USPC .......................................................... 606/99

(58) Field of Classification Search
USPC ................ 606/86 A, 99, 914, 207, 238
See application file for complete search history.

(56) References Cited

U.S. PATENT DOCUMENTS

| | | | |
|---|---|---|---|
| 6,648,888 B1* | 11/2003 | Shluzas | 606/86 A |
| 6,805,716 B2* | 10/2004 | Ralph et al. | 623/17.16 |
| 7,115,132 B2* | 10/2006 | Errico et al. | 606/86 R |
| 7,235,082 B2* | 6/2007 | Bartish et al. | 606/99 |
| 2001/0021853 A1* | 9/2001 | Heckele et al. | 606/99 |
| 2002/0045904 A1* | 4/2002 | Fuss et al. | 606/99 |
| 2004/0010261 A1* | 1/2004 | Hoag et al. | 606/99 |
| 2006/0235426 A1* | 10/2006 | Lim et al. | 606/99 |
| 2007/0067035 A1* | 3/2007 | Falahee | 623/17.11 |
| 2007/0093850 A1* | 4/2007 | Harris et al. | 606/99 |
| 2007/0162128 A1* | 7/2007 | DeRidder et al. | 623/17.11 |
| 2007/0260314 A1* | 11/2007 | Biyani | 623/17.11 |
| 2008/0125865 A1* | 5/2008 | Abdelgany | 623/17.16 |

\* cited by examiner

*Primary Examiner* — Christian Sevilla
(74) *Attorney, Agent, or Firm* — Rahman LLC

(57) ABSTRACT

A surgical tool for inserting an implant in a vertebral body. The surgical tool includes a shaft with a shaft thread adapted to engage the implant, a piston coupled to the shaft thread to articulate the implant from a starting linear position to a final curvilinear position, an actuator coupled to the piston to adjust a position of the implant, and an annular structure surrounding the shaft to increase a stability of an end part of the implant on an impact of insertion. A screw attached to the piston may lock the end part of the implant. A lock lever may lock the position of the piston in at least one position, and a knob may disengage the implant from the surgical tool.

20 Claims, 16 Drawing Sheets

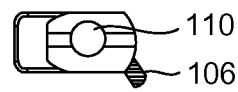
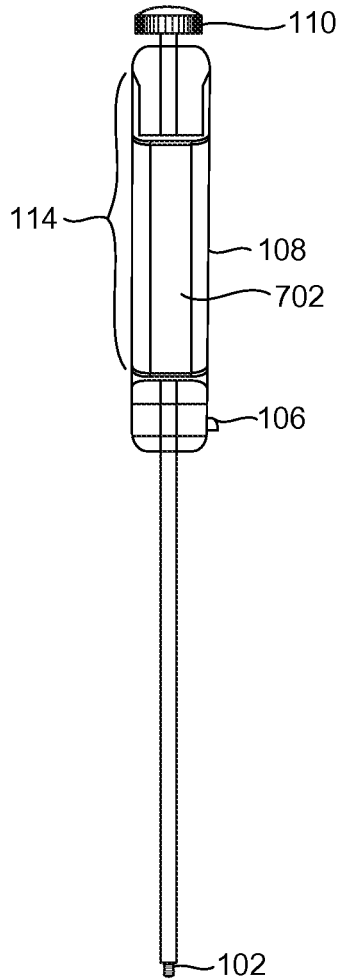
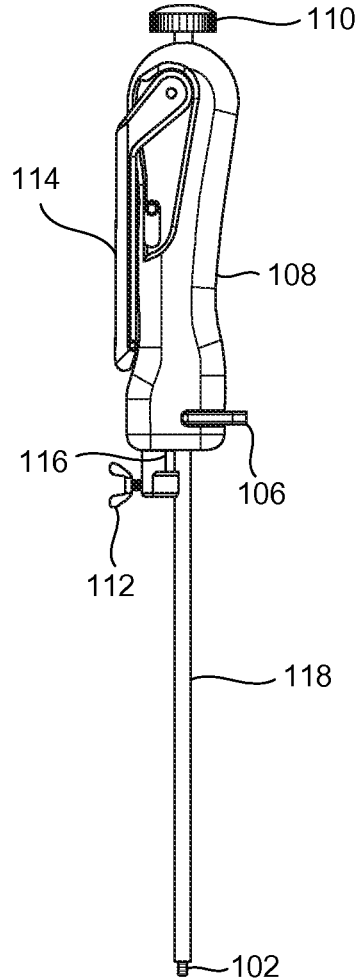
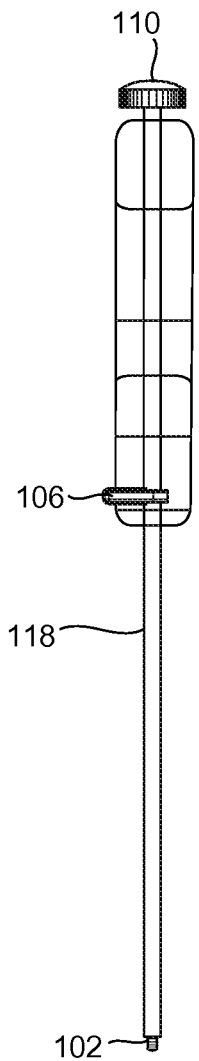
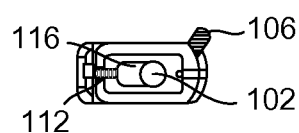
FIG. 6D
FIG. 6B
FIG. 6A
FIG. 6C
FIG. 6E

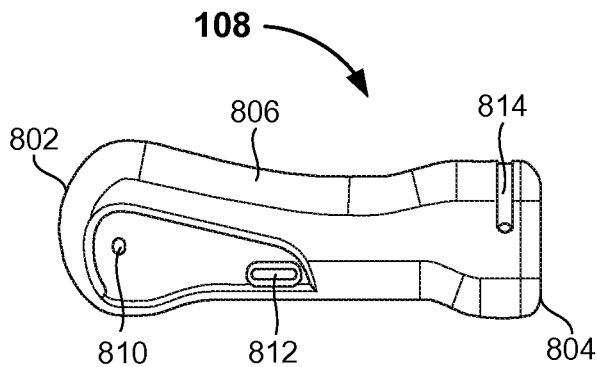
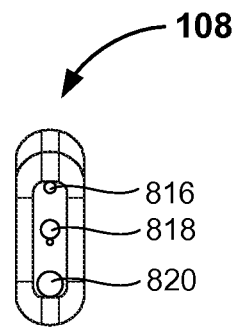
FIG. 8B        FIG. 8E
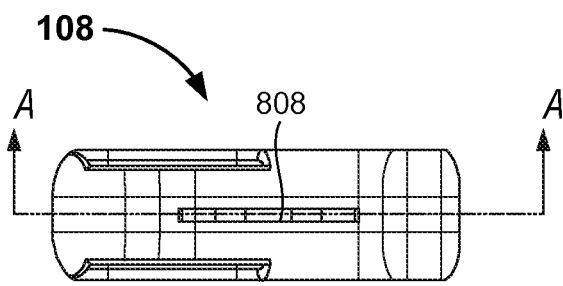
FIG. 8C
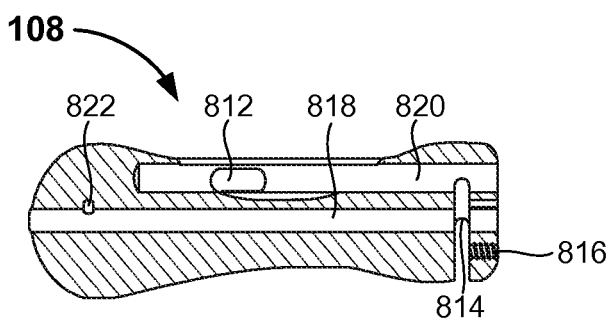
FIG. 8D
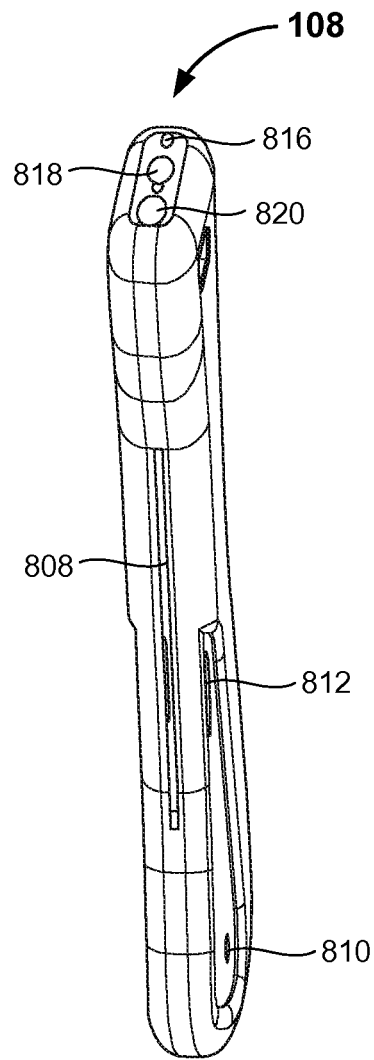
FIG. 8A

INSERTER DEVICE USED FOR ORTHOPEDIC SURGERY

BACKGROUND

1. Technical Field

The embodiments herein generally relate to medical devices, and, more particularly, to inserter devices used during orthopedic surgeries.

2. Description of the Related Art

As a natural part of the aging process, disks or vertebrae become less supple and more prone to damage. Disks can also degenerate, losing mass and thickness, allowing vertebrae to contact each other. This can pinch nerves, be painful and greatly affect the quality of one's life. Disk-related pain is very common in the neck, which is subject to constant twisting forces, and the lower back, which experiences large compressive forces. To prevent the nerves from being damaged, and to treat back pain even when the anatomical source of the problem cannot be located, spinal fusion is used. Spinal fusion is a surgical technique used to unite two or more vertebrae. Supplementary bone tissue is used along with the body's natural cells responsible for bone formation. This procedure may eliminate abnormal motion of the vertebrae by restricting their movement.

Spinal fusion is typically performed in the lumbar region, but may also be performed on thoracic vertebrae or vertebrae immediately behind the skull. Spinal fusion surgery may be approached posteriorly (e.g., from the back) or anteriorly (e.g., through the abdomen). According to the American Academy of Orthopedic Surgeons, approximately a quarter-million spinal fusions are performed each year. Fusion may involve use of instrumentation such as plates, screws and cages, and bone or bone substitutes to get the vertebrae to fuse together. The bone may be taken either from another bone in the patient's body (e.g., autograft) or from a bone bank (e.g., allograft).

Lumbar spinal fusion may be of two types, posterolateral fusion and interbody fusion. In interbody fusion, an implant may be placed between vertebrae in the area usually occupied by an intervertebral disc. The disc is removed entirely and the implant may be placed between the vertebra to maintain spinal alignment and disc height. The fusion then occurs between the endplates of the vertebrae. Two types of interbody fusion are anterior lumbar interbody fusion (ALIF), in which an anterior abdominal incision is used to reach the lumbar spine and posterior lumbar interbody fusion (PLIF), in which a posterior incision is used to reach the lumbar spine.

In order to accomplish implant insertion, inserter devices may be used by persons performing the spinal fusion surgery (e.g., surgeons). The success of an interbody fusion procedure (e.g., PLIF) may depend largely on parameters such as orientation of the implant during insertion, impact forces, ease of release of implant from the inserter device, and the position in which the implant is fixed between the vertebrae. Conventional inserter devices offer limited maneuverability and control over implant orientation and impact forces. Usage of such devices may lead to complications or failures despite high skill levels of surgeons. Further, due to a lack of control of impact forces, implants may be crushed or bent during insertion. Accordingly, there remains a need for a new tool to allow surgeons to perform spinal surgeries with minimum risk, and increased control and ease.

SUMMARY

In view of the foregoing, an embodiment herein provides a surgical tool for inserting an implant in a vertebral body, wherein the tool includes a shaft with a shaft thread at one end of the shaft to engage the implant, a piston coupled to the shaft thread to transmit an action to the implant, an actuator coupled to the piston to adjust a position of the implant, and an annular structure (e.g., a C-ring) surrounding the shaft to increase a stability of an end part of the implant on an impact of insertion. A screw may be attached to the piston to lock the end part of the implant. A lock lever may lock the position of the piston in at least one position, and a knob at another end of the shaft may disengage the implant from the surgical tool on rotation of the knob.

In another aspect, a method of performing a surgical procedure includes engaging an implant having at least two parts that are rotatable with respect to each other, adjusting a position of the implant so that a first part of the implant is tilted to an intermediate curvilinear position, and upon insertion of the implant into a vertebral body, disengaging an end part of the implant from the surgical inserter device. Initially, the implant may be maintained (e.g., locked) in a starting linear position so that all of the at least two parts of the implant are aligned to each other. Upon adjusting the position of the implant to the intermediate curvilinear position, the implant may be maintained in an intermediate position. Finally, the position of the implant may be adjusted so that a second part of the implant is tilted to a final position, in which it may be maintained.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIGS. 6A through 6E illustrate a front view, left side view, right side view, top view, and bottom view respectively of the inserter device of FIG. 1 according to an embodiment herein;

FIGS. 8A through 8E illustrate a perspective view, front view, side view, cross-sectional view, and bottom view respectively of the body of the inserter device of FIG. 1 according to an embodiment herein;

DETAILED DESCRIPTION OF PREFERRED EMBODIMENTS

Figure 1:
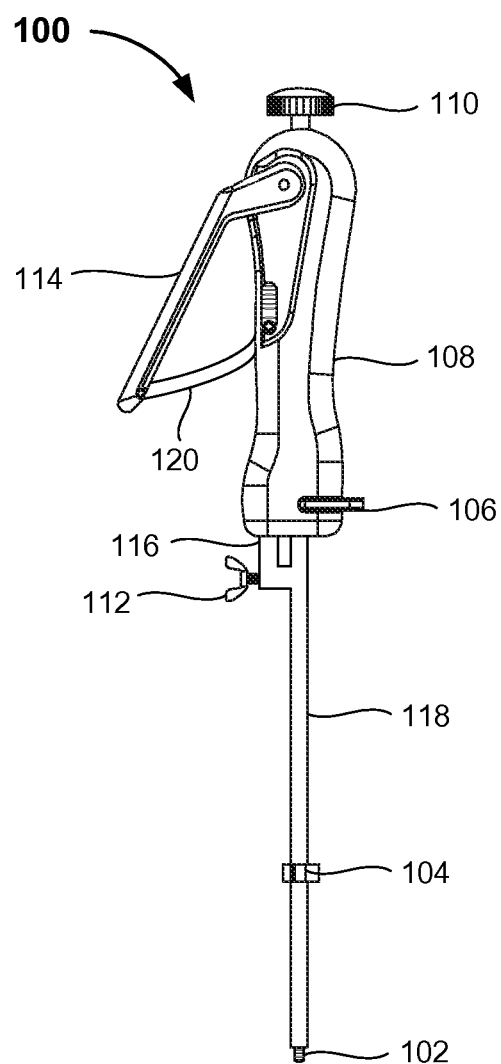
FIG. 1 illustrates a general view of an inserter device according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a new tool to allow surgeons to perform spinal surgeries with minimum risk, and increased control and ease. The embodiments herein achieve this by providing a surgical tool for inserting an implant that may include a shaft with a shaft thread adapted to engage the implant, a piston coupled to the shaft thread to articulate the implant from a starting linear position to a final curvilinear position, an actuator coupled to the piston to adjust a position of the implant, and an annular structure surrounding the shaft to increase a stability of an end part of the implant on an impact of insertion. Referring now to the drawings, and more particularly to FIG. 1 through FIG. 16, where similar reference characters denote corresponding features consistently throughout the figures, there are shown preferred embodiments.

Figure 15:
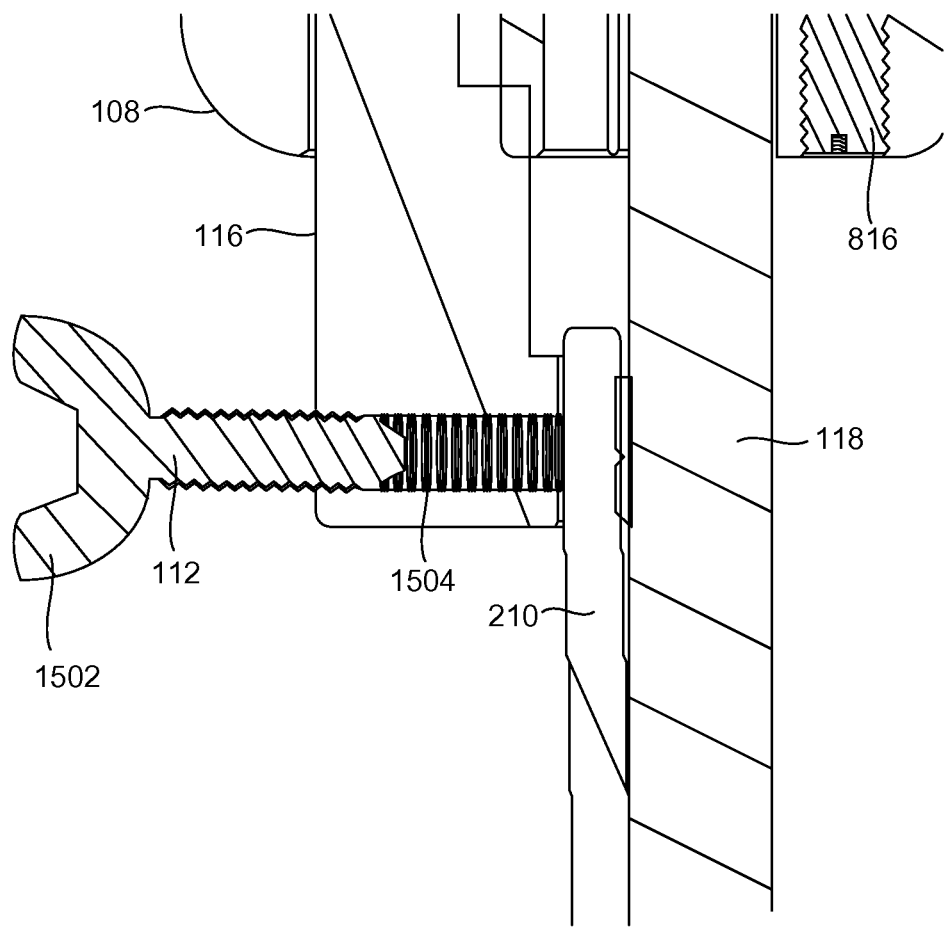
FIG. 15 illustrates a magnified sectional view of a portion of the inserter device of FIG. 1 according to an embodiment herein.

FIG. 1 illustrates a general view of an inserter device 100 having a shaft thread 102, a C-ring 104, a lock lever 106, a body 108, a knob 110, a lock screw 112, an actuator 114, a piston 116, a shaft 118, and a link 120 according to an embodiment herein. The shaft thread 102 may be positioned at one end of the inserter device 100, and provides a threading mechanism for engaging an implant 200 (shown in FIGS. 2 through 4) (e.g., an implant to be inserted into a vertebral column as part of a spinal fusion procedure). The shaft 118 may be connected to the shaft thread 102 at one end of the shaft 118, and may have a knob 110 at the opposite end. The shaft 118 may extend through a body 108 for stable connection to the body 108. An annular structure such as the C-ring 104 may surround the shaft 118 at a position between the body 108 and the shaft thread 102. The piston 116 may have one end that is attached to the link 120 inside the body 108. The other end of the piston 116 may extend from the body 108 and be connected to the shaft 118. The lock screw 112 may pass through the end of the piston that extends from the body 108 (e.g., through the socket 1208 as shown in FIGS. 12A through 12D) to make contact with a wire 210 of FIG. 2 (e.g., by the threaded end 1504 as shown in FIG. 15). The lock lever 106 may extend from the body 108 in the side opposite to that of the lock screw 112 to make contact with the piston 116 (e.g., through the rectangular grooves 1210 and 1212 of the piston 116 shown in FIG. 12B). The link 120 may connect the actuator 114 to the piston 116 and pass through the body 108 (e.g., through the socket 808 as shown in FIG. 8A and FIG. 8C) during rotation of the actuator 114.

Figure 2:
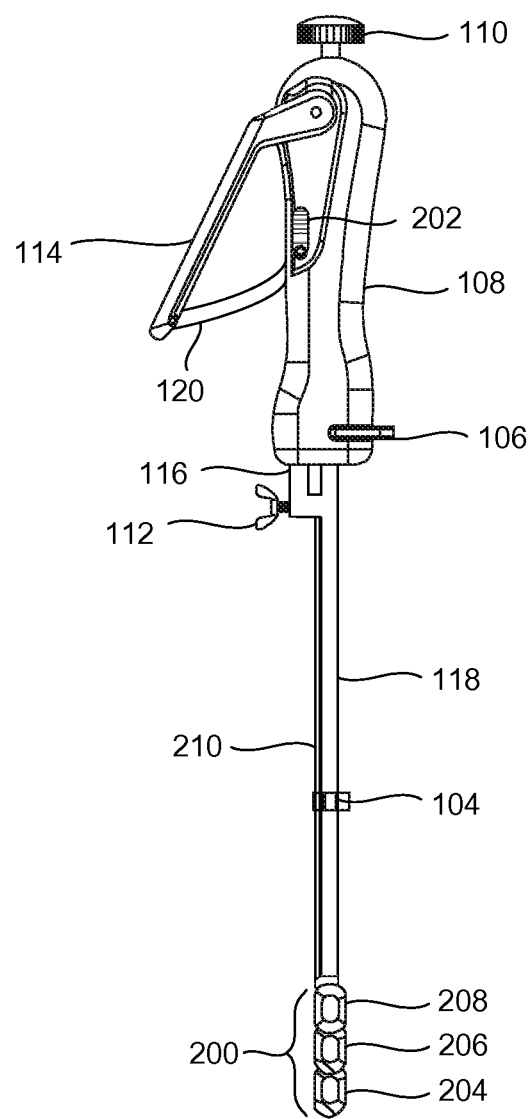
FIG. 2 illustrates the inserter device of FIG. 1 engaging an implant at a starting position according to an embodiment herein.
Figure 4:
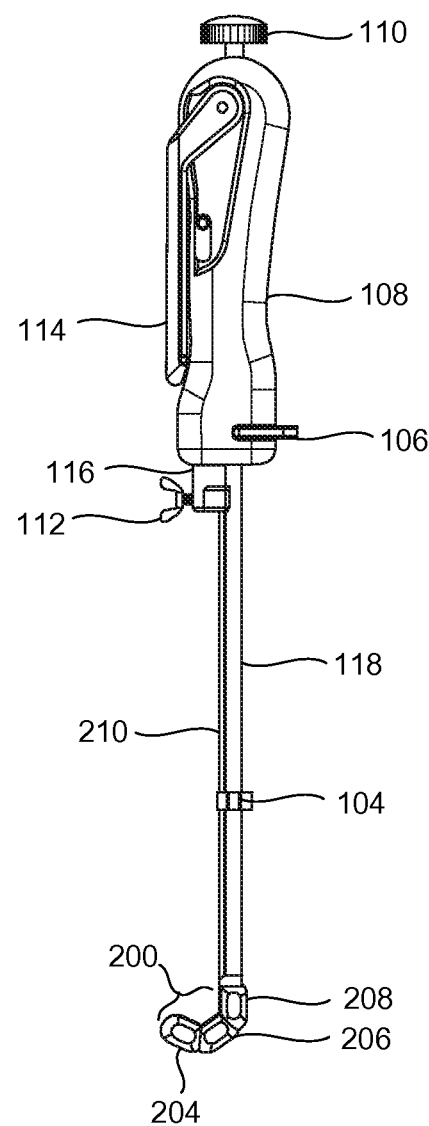
FIG. 4 illustrates the inserter device of FIG. 1 engaging an implant at a final position according to an embodiment herein.
Figure 5:
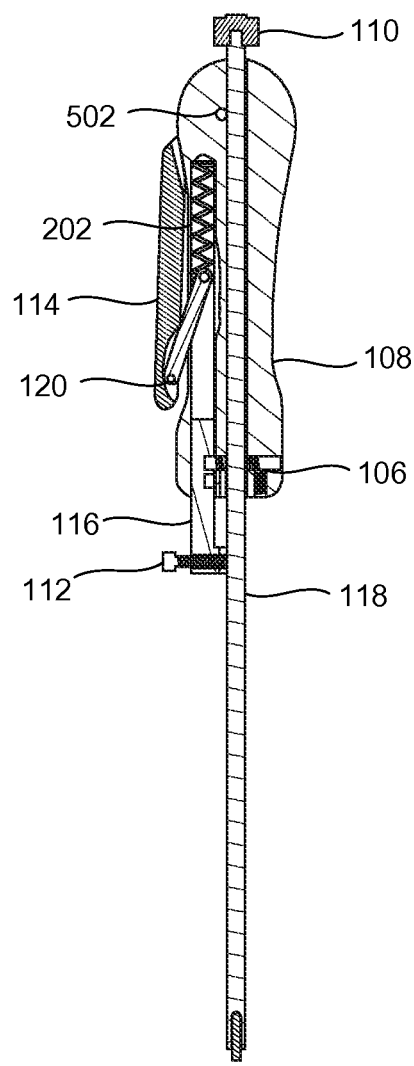
FIG. 5 illustrates a sectional view of the inserter device of FIG. 1 according to an embodiment herein.
Figure 7B:
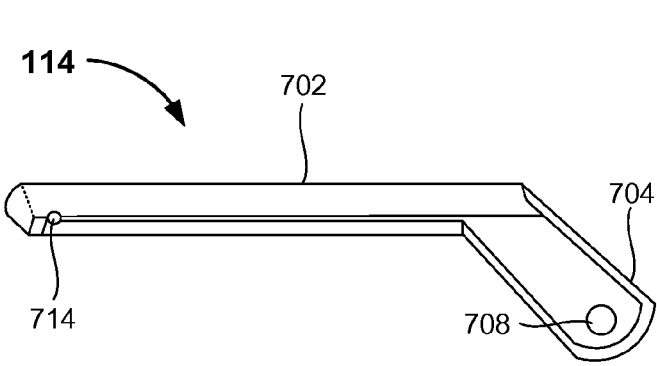
FIGS. 7A through 7E illustrate a perspective view, front view, back view, side view, and top view respectively of the actuator of the inserter device of FIG. 1 according an embodiment herein.
Figure 7A:
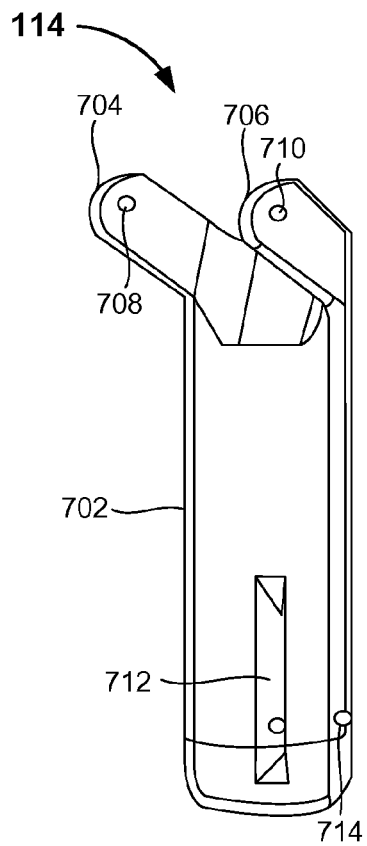
Figure 7D:
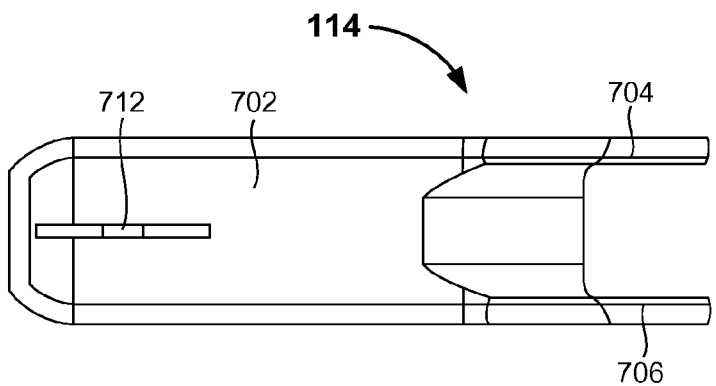
Figure 7C:
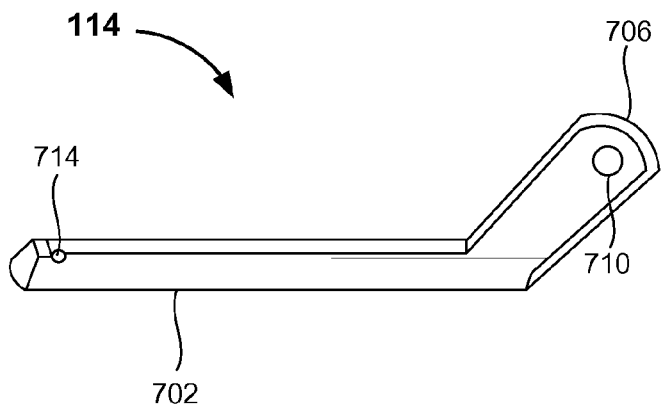
Figure 7E:
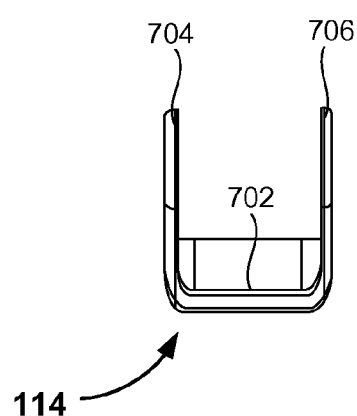

The actuator 114 may extend from the body 108 (e.g., connected to the body 108 through the first arm 704 and the second arm 706 of the actuator 114 shown in FIGS. 7A, 7D, and 7E) towards the same side of the body 108 as that of the lock screw 112 to be connected to the end of the link 120 opposite to the end that is attached to the piston 116. The actuator 114 may be rotated by a user (e.g., a surgeon) to adjust a position of the implant 200. The amount of the rotation may determine the position of the implant 200. The rotation of the actuator 114 may transmit an action to the piston 116 (e.g., through the link 120 and the spring 202 as shown in FIG. 5). The lock lever 106 may be rotated to lock the actuator 114 at one or more positions (e.g., a starting position, an intermediate position, and/or a final position). The body 108 may be gripped by the user to manipulate the inserter device 100 during implant insertion FIG. 2 illustrates a starting position of the inserter device 100 of FIG. 1 according to an embodiment herein. The inserter device 100 is shown to be engaging an implant 200. The implant 200 is illustrated as having a first part 204, a second part 206, and a third part 208, in which the first part 204 is rotatable with respect to the second part 206, and the second part 206 is rotatable with respect to the third part 208 (e.g., as shown in FIG. 4); however in various other embodiments the implant 200 may have only two parts or more than three parts. The inserter device 100 may also include a spring 202 inside the body 108 that is connected to top end of the piston 116 (e.g., as shown in FIG. 5). A wire 210 is positioned parallel to the shaft 118 (e.g., shown in FIGS. 2 through 4).

Figure 12D:
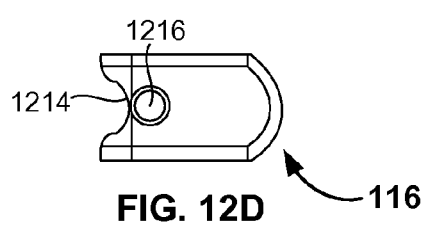
FIGS. 12A through 12D illustrate a perspective view, front view, side view, and bottom view respectively of the piston of the inserter device of FIG. 1 according to an embodiment herein.
Figure 12B:
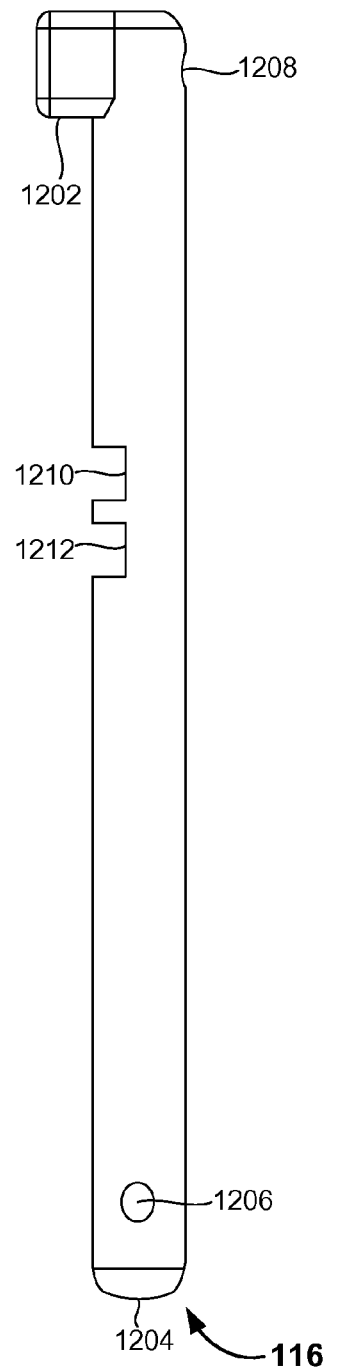

The starting position of the inserter device 100 may correspond to a starting position of the implant 200 in which all parts of the implant 200 are aligned to each other in a linear fashion. At the starting position, the actuator 114 may be positioned at a maximum angle to the longitudinal axis of the shaft 118. The end of the link 120 that is connected to the actuator 114 is at a highest position, and the opposite end of the link 120 that is connected to the piston 116 is at a lowest position. Further, the spring 202 is in a relaxed or least compressed state so as not to exert a restoring force on the piston 116. In one embodiment, the lock lever 106 may lock the actuator 114 by locking the piston 116 (e.g., through the groove 1212 of FIG. 12B) when the inserter device 100 is in the starting position. Once the groove 1212 of FIG. 12B is at a desired position, the lock lever 106 may rotate and hold the position to maintain the implant 200 in a corresponding starting position so that the first part 204, the second part 206, and the third part 208 are aligned to with respect to one another.

Figure 3:
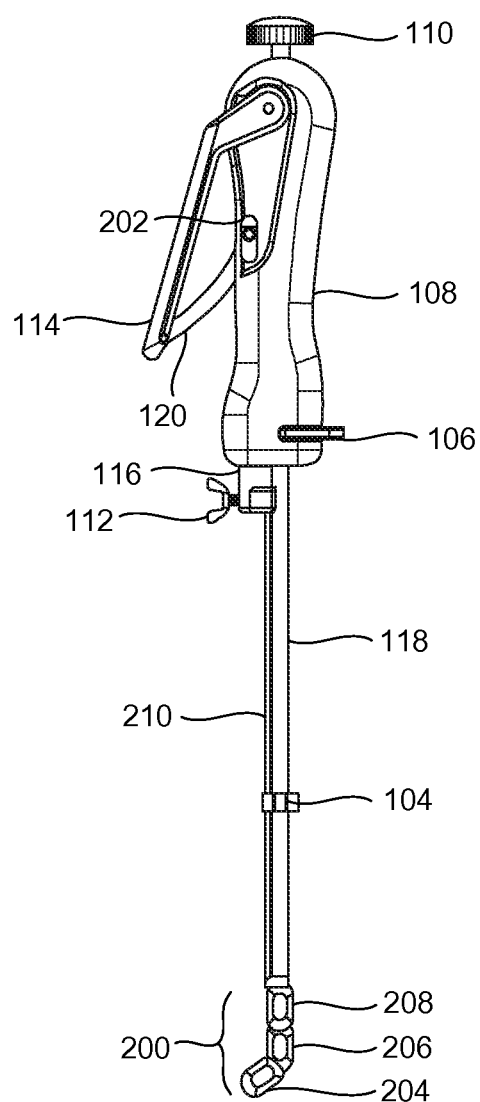
FIG. 3 illustrates the inserter device of FIG. 1 engaging an implant at an intermediate position according to an embodiment herein.

FIG. 3 illustrates an intermediate position of the inserter device 100 of FIG. 1 according to an embodiment herein. The position of the actuator 114 may be adjusted (e.g., rotated) towards the shaft 118 to get to the intermediate position of the inserter device 100 in which the angle between the longitudinal axis of the shaft 118 and the actuator 114 is less than that of the starting position (e.g., in between that in the starting position of FIG. 2 and a final position as shown in FIG. 4). Upon rotation of the actuator 114, the end of the link 120 that is connected to the actuator 114 is at a lower position than the opposite end of the link 120 that is connected to the piston 116, which is at a higher position as compared to the starting position. Further, the spring 202 is in a partially compressed state so as to exert a restoring force on the piston 116, which is then raised.

Figure 14:
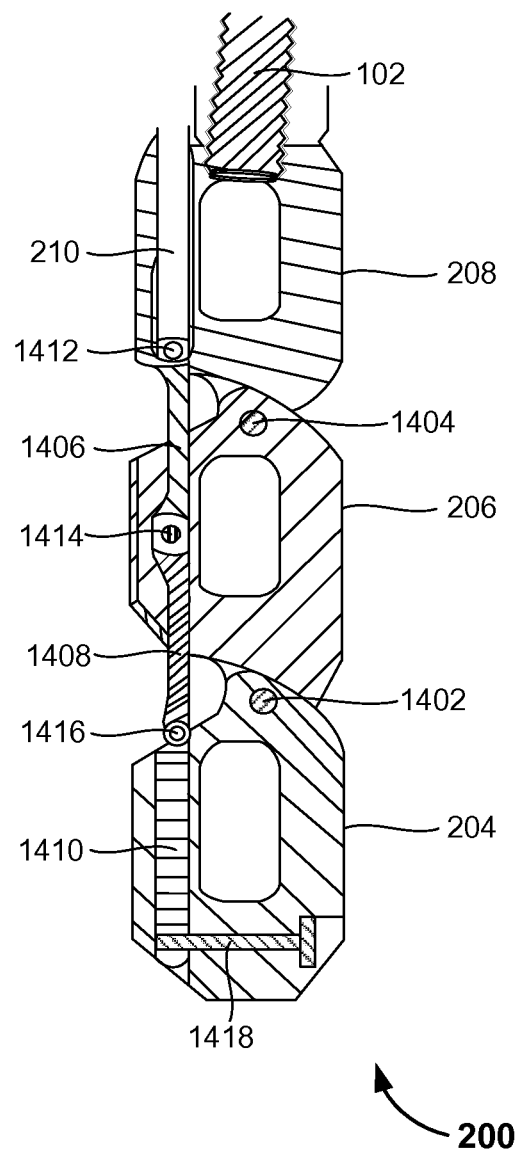
FIG. 14 illustrates a sectional view of the implant of FIG. 2 connected to the shaft thread and the wire of the inserter device of FIG. 2 according to an embodiment herein.

The wire 210 at its upper end is attached to the piston 116 and the bottom end is connected to the first part 204 of the implant 200 (e.g., as shown in FIG. 14). Therefore when the piston 116 is translated, the wire 210 transmits the action that causes the implant 200 to bend because the implant 200 is made of rotatable links 204, 206, 208. The wire 210, being rigid, makes the implant 200 assume the intermediate and final curvilinear positions. However, the lock screw 112 may lock and keep the wire 210 remain aligned adjacent to the shaft 118 (e.g., by the threaded end 1504 as shown in FIG. 15) thereby maintaining the third part 208 of the implant 200 locked thereby causing it to remain aligned to the shaft 118. Thus, the implant 200 is adjusted to a corresponding intermediate position so that the first part 204 is inclined with respect to the second part 206 and a third part 208, whereas the second part 206 and the third part 208 are aligned with each other. In one embodiment, the lock lever 106 may lock the actuator 114 by locking the piston 116 (e.g., through the groove 1210 of FIG. 12) when the inserter device 100 is in the intermediate position. Once the groove 1210 of FIG. 12 is at a desired position, the lock lever 106 may rotate and hold the position to maintain the implant 200 in a corresponding intermediate position.

FIG. 4 illustrates a final position of the inserter device 100 of FIG. 1 according to an embodiment herein. The position of the actuator 114 may be adjusted (e.g., rotated) towards the shaft 118 to get to the final position of the inserter device 100 in which the angle between the longitudinal axis of the shaft 118 and the actuator 114 is minimum (e.g., the actuator 114 may be parallel to the shaft 118, and the actuator 114 may touch the body 108). Upon rotation of the actuator 114, the end of the link 120 that is connected to the actuator 114 is at a lowest position, and the opposite end of the link 120 that is connected to the piston 116 is at a highest position. Further, the spring 202 is in a state of maximum compression state so as to exert a high restoring force on the piston 116, which is then raised to a maximum level. This action of the piston 116 may be translated to the third part 208 of the implant. However, the lock screw 112 may lock the wire 210 (e.g., by the threaded end 1504 of FIG. 15) so that the third part 208 of the implant 200 remains aligned to the shaft 118.

Thus, the implant 200 is adjusted to a corresponding final position so that the second part 206 is inclined with respect to the third part 208, and the first 204 part is inclined with respect to the second part 206. In one embodiment, the lock lever 106 may lock the actuator 114 (e.g., by locking the piston 116 in the second groove 1210 as shown in FIG. 12B) and maintain the implant 200 in the final position. The C-ring 104 may prevent the end (e.g., third part 208) part of the implant 200 from bending under pressure of an impact force. Once the implant 200 is fully inserted, the body 108 may be rotated by 30 degrees (e.g., about the axis as shown in FIG. 8C) In addition, the third part 208 of the implant may be released by rotating the knob 110 (e.g., by rotating the knob 110 counter-clockwise by a user gripping the outer gripping surface 1006 of FIGS. 10A, 10C and 10D, the shaft 118 may disengage the third part 208 of the implant 200 via the shaft thread 102).

FIG. 5 illustrates a sectional view of the inserter device 100 according to an embodiment herein. The shaft 118 may be capped with the knob 110 (e.g., through the attachment head 902 of FIG. 9A) and may include a threading mechanism (e.g., the shaft thread 102) at the base of the shaft 118. The handle dowel pin 502 may be inserted (e.g., as explained below in reference to FIGS. 8A through 8E) to fix the shaft 118 after the shaft 118 is attached (e.g. through the groove 904 of FIG. 9A) with the body 108 in such a manner as to prevent any longitudinal movement of the shaft 118.

The actuator 114 may be connected with the body 108 at one end and with the link 120 at the opposing end. The piston 116 may be coupled with the link 120 at the proximal end and with the shaft 118 at the distal end. The lock screw 112 may both fix the piston 116 with the shaft 118 and lock the end part 204 of the implant 200. The inserter shaft 118 may also attach to a spring 202 which may recline above the piston 116 connecting with the link 120. The spring 202 may provide the force needed to make the piston 116 move. The lock lever 106 may lock the position of the piston 116 with the grooves 1210 and 1212 (of FIG. 12B) configured therein. The body 108 may incorporate almost all the components; e.g., lock lever 106, actuator 114, piston 116, link 120 and the handle dowel 502. Preferably, the shaft 118 revolves (e.g., clockwise, anti-clockwise) by the help of the knob 110.

FIGS. 6A through 6E illustrate various views of the inserter device 100 of FIG. 1 according to an embodiment herein. FIG. 6A is the front view of the inserter device 100 which illustrates the shaft thread 102, the lock lever 106, the body 108, the knob 110, the lock screw 112, the actuator 114, the piston 116 and the shaft 118. Here, the actuator 114 is in the final position and the piston 116 is in the upward position with the support of the lock lever 106 (as described above with respect to FIG. 4). FIG. 6B is the left side view of the inserter device 100 illustrating the shaft thread 102, lock lever 106, the body 108, the knob 110, the lock screw 112, the actuator 114, and the piston 116. The body 108 may appear as a rectangular structure with rounded corners, although other geometric configurations are possible. In the left side view, the top portion of the body 108 is shown, the rectangular plate 702 (as further shown in FIGS. 7A through 7E) of the actuator 114 and the lock lever 106. FIG. 6B illustrates the lock screw 112 which may be a rounded structure below the body 108. FIG. 6C is the right side view of the inserter device 100 illustrating the shaft thread 102, the lock lever 106, the knob 110, and the shaft 118. The body 108 in the right side view of FIG. 6C may be a rectangular structure, although other configurations are possible, and the only part visible in the body 108 is the lock lever 106 in this view. FIG. 6D is the top view of the inserter device 100 showing the lock lever 106 and the knob 110. FIG. 6E is the bottom view of the inserter device 100, which may possess the shaft thread 102, the lock lever 106, the lock screw 112, and the piston 116.

FIGS. 7A through 7E illustrate various views of the actuator 114 of the inserter device 100 of FIG. 1 according to an embodiment herein. FIG. 7A is the perspective view of the actuator 114. As shown, the actuator 114 of the inserter device 100 may have an elongated rectangular plate 702 having a first and second arm 704, 706 respectively attached at the upper end of the actuator 114. The arms 704 and 706 may be attached to the edge of the plate 702 separated by a distance equaling the width of the plate. Each of the two arms 704 and 706 may include bores 708 and 710 respectively. The actuator 114 may also include another hollow portion 712 at the inner lower end of the plate parallel to both vertical sides of the plate 702. There may be another aperture 714 on the horizontal side of the actuator 114. FIGS. 7B and 7C are the front view and the back view of the actuator 114 respectively which illustrate the actuator 114 in an angular shape (e.g., hockey stick) having rectangular plate 702, a bore 710, and an aperture 714. FIG. 7D is the side view of the actuator 114 with plate 702 and having a curved shape (e.g. "U" shape) on the upper end and the two corners of the bottom may be slightly curved. The side view of FIG. 7D also illustrates the arms 704, 706 and the hollow portion 712. FIG. 7E is the top view of the actuator 114 illustrating a curved shape (e.g. "U" shape) with a rectangular plate 702 and the arms 704, 706.

The bores 708 and 710 on the upper end of the plate 702 of actuator 114 may connect the actuator 114 to the handle or body 108 of the inserter device 100 (e.g. through the hole 810 of FIGS. 8A and 8B). The actuator 114 of the inserter device 100 may be coupled to one end of the link 120 through the aperture 714 (e.g., through the bore 1106 of FIGS. 11A through 11C), the other end of the link 120 being connected to the piston 116 (e.g. through the opening 1206 of FIGS. 12A and 12B) by the help of a spring 202 (shown in FIG. 5). Therefore, when the actuator 114 is rotated, it may move or control the piston 116. The hollow portion 712 may be present at the inner lower end of the plate 702, which allows the link 120 to move through it.

FIGS. 8A through 8E illustrate various views of the body 108 of the inserter device 100 according to an embodiment herein. FIG. 8A is the perspective view of the body 108 of the inserter device 100 of FIG. 1 illustrating a slightly rounded head 802 and a dice shaped opposing end 804 and a core part 806 that may be slightly narrowed (e.g., bone shaped). An elongated hollow portion 808 may be centered on one side of the body 108. The upper end 802 of the body 108 may include a hole 810 at the adjacent side to that of the hollow portion 808. There may be another bean shaped slot 812 present at a somewhat central portion of the body 108. The bottom 804 of the body 108 may also possess a bullet shaped gap 814. Three spherical openings 816, 818, and 820 may be present at the bottom portion of the body 108 out of which the opening 818 may be positioned between the other two openings 816 and 820. FIG. 8B is the front view of the body 108 that illustrates the rounded head 802, a dice shaped opposing end 804 and a slightly narrowed center 806. The front view may also include a hole 810, a bean shaped slot 812 and another bullet shaped gap 814. FIG. 8C is the side view showing a four sided figure having somewhat rounded corners with the hollow portion 808 at the center of the axis. FIG. 8D is the sectional view taken along line A-A of FIG. 8C illustrating the bean shaped slot 812, the bullet shaped gap 814, the cylindrical gap 818, a rectangular slit 820, the opening 816, and the opening 822. FIG. 8E is a bottom view which shows the body 108 having the shape of a dice which may include the spherical openings 816, 818, and 820.

The hollow portion 808 may allow for the movement of the link 120 which is attached to the piston 116 of the inserter device 100 (e.g., through the bore 1104 of FIGS. 11A through 11C and opening 1206 of FIGS. 12A and 12B) and a fastener (e.g., a pin) (not shown) passing through the hole 810 may fix the actuator 114 to the body 108 (e.g., through the bores 708, 710 of FIGS. 7A through 7C). The bean shaped slot 812 may be present for the spring 202 to rest in, which may then connect to the link 120. The lock lever 106 may be connected to the body 108 by the bullet shaped gap 814. The purpose of the openings 818 and 820 may be for extending the length of the shaft 118 and for passing the piston 116 respectively throughout the body 108. There may be a screw (not shown), which passes through the opening 816, and may fix the lock lever 106 into position. The opening 822 may allow the passage of the handle dowel pin 502 to fix the shaft 118 after the shaft 118 is attached (e.g., as shown in FIG. 5) to the body 108.

Figure 9A:
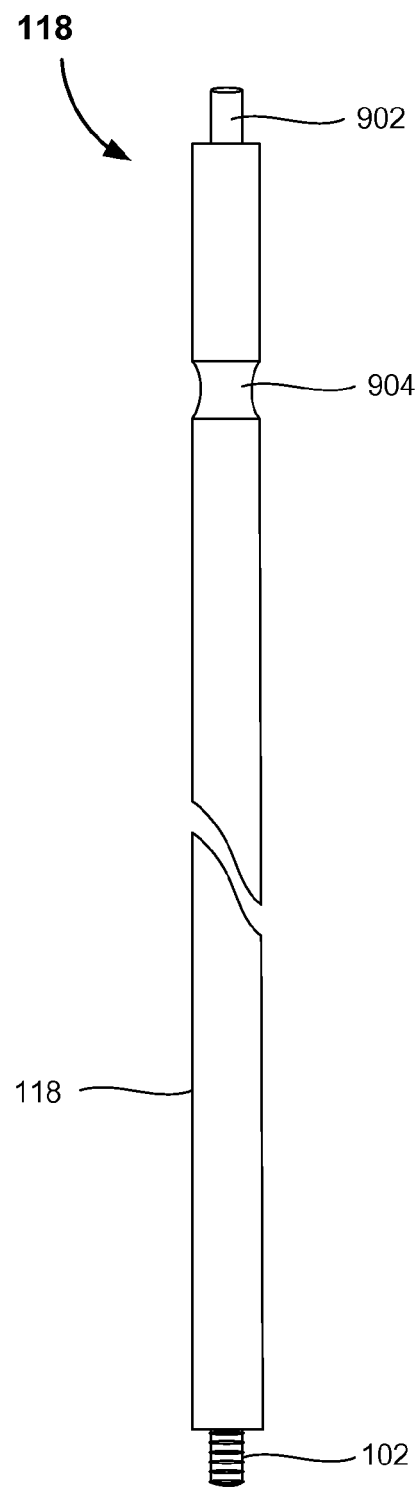
FIGS. 9A and 9B illustrate a front view and bottom view respectively of the shaft of the inserter device of FIG. 1 according to an embodiment herein.
Figure 9B:

FIG. 9A and FIG. 9B illustrate a front view and bottom view of the shaft 118 of the inserter device 100 according to an embodiment herein. FIG. 9A is the front view of the shaft 118 illustrating an elongated rectangular structure with a cuboid attachment head 902 at the upper end, a compressed groove 904 configured below the head 902, and a cylindrical shaft thread 102 at the distal end of the shaft 118. The attachment head 902 and the groove 904 may have a smaller diameter than the shaft 118. FIG. 9B is a bottom view of the shaft 118 illustrating the respective diameters of the shaft thread 102 and the shaft 118. The shaft 118 may be connected to the threading mechanism (e.g., the shaft thread 102) at one end of the shaft 118 and a knob 110 at another end of the shaft 118 to disengage the implant 200 from the inserter 100. The attachment head 902 may be connected into the knob 110 (e.g. through the aperture 1004 of FIGS. 10A through 10C) and the groove 904 may be connected to the handle dowel pin 502 to fix the shaft 118 (e.g. as shown in FIG. 5). The shaft thread 102 connects to the implant 200.

Figure 10C:
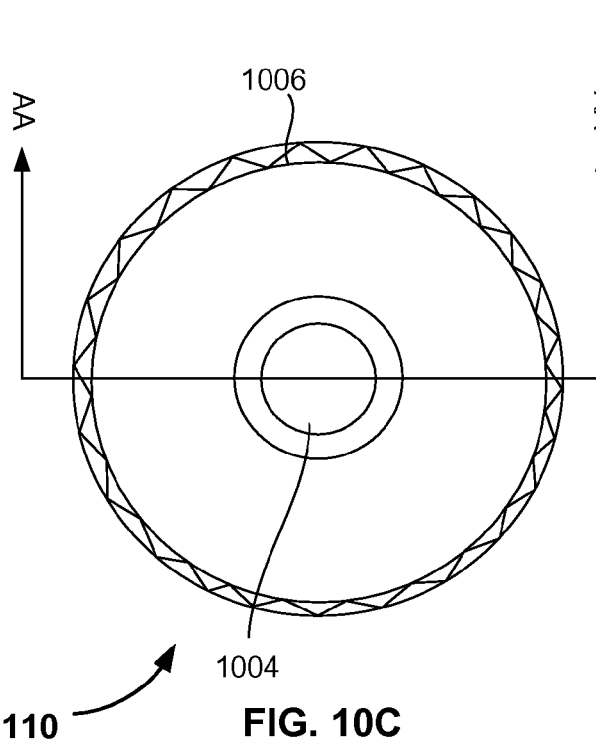
FIGS. 10A through 10D illustrate a perspective view, cross-sectional view, bottom view, and side view respectively of the knob of the inserter device of FIG. 1 according to an embodiment herein.
Figure 10D:
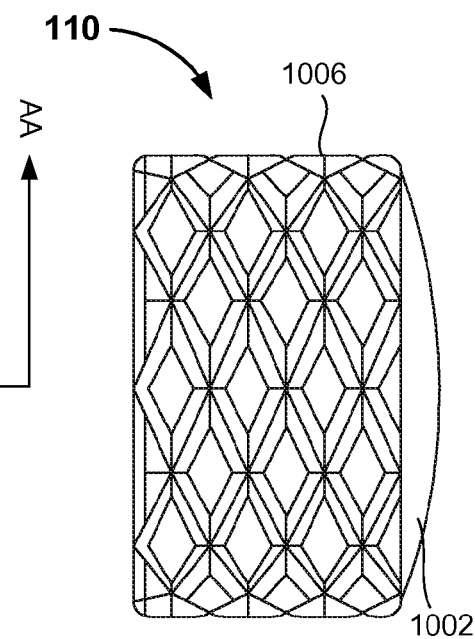
Figure 10B:
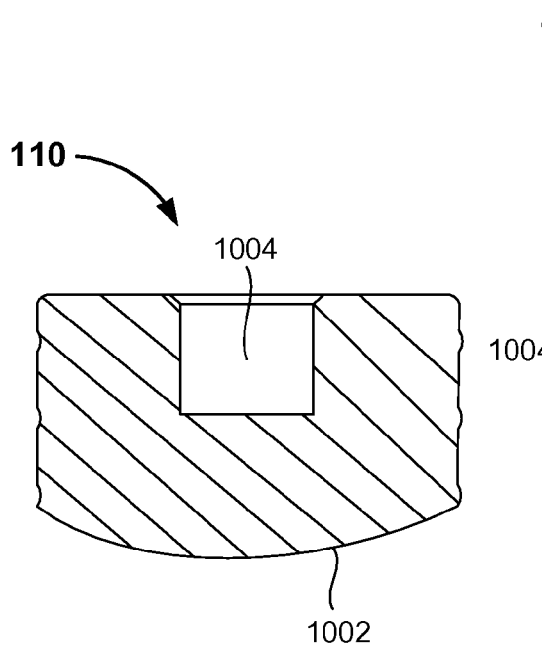
Figure 10A:
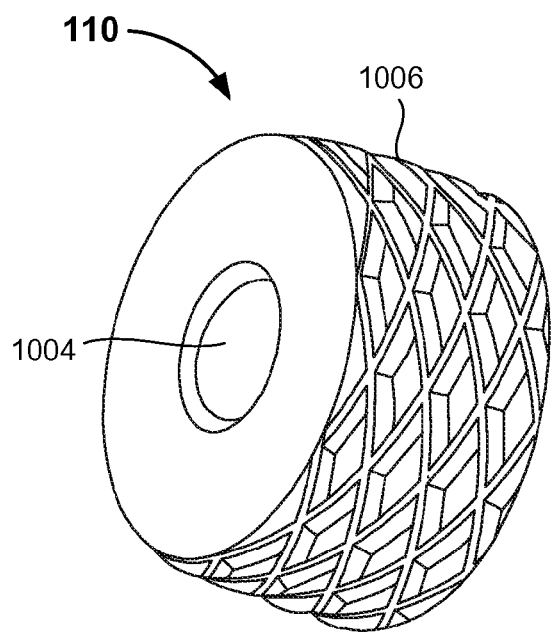

FIGS. 10A through 10D illustrate various views of the knob 110 of the inserter device 100 of FIG. 1 according to an embodiment herein. FIG. 10A is the perspective view which illustrates a two-dimensional view of the knob which includes an inner aperture 1004 and an outer gripping surface 1006. FIG. 10B is the sectional view of the knob 110 taken along line AA-AA of FIG. 10C and illustrating the knob 110 to have a generally rectangular shape with a convex surface 1002. The knob 100 also includes an aperture 1004. FIG. 10C is the bottom view illustrating the inner aperture 1004 and an outer circle 1006 centered at one point along the same axis. The outer diameter may be the same as that of the closed convex surface 1002 and larger than the inner diameter of the aperture 1004. FIG. 10D is the side view showing an outer gripping surface 1006 and a convex surface 1002 at the right side. The knob 110 may have a tubular shape which may include a closed convex top 1002 and an opposing end closed having an aperture 1004 formed therein. The inner diameter of the aperture 1004 may be sufficiently large to accommodate the shaft 118 (e.g., by the attachment head 902 of FIG. 9A) and the outer gripping surface 1006 may be used as a handgrip. The knob 110 may disengage the implant 200 from the inserter device 100 upon rotation.

Figure 11B:
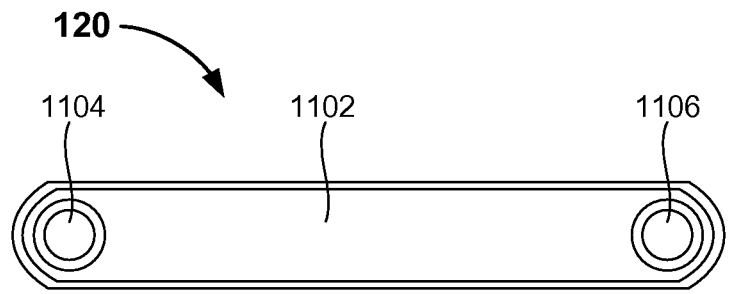
FIGS. 11A through 11C illustrate a perspective view, front view, and side view respectively of the link of the inserter device of FIG. 1 according to an embodiment herein.
Figure 11C:
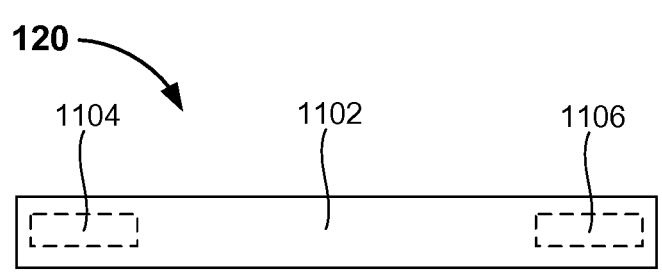
Figure 11A:
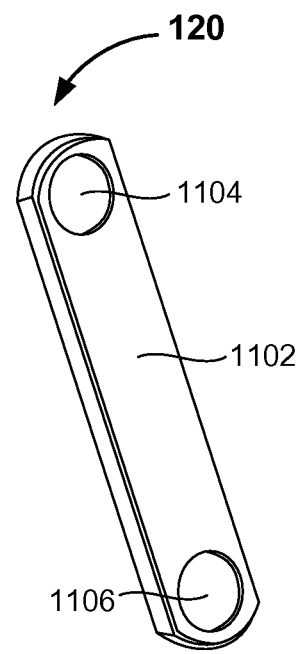

FIGS. 11A through 11C illustrate various views of the link 120 of the inserter device 100 of FIG. 1 according to an embodiment herein. FIG. 11A is the perspective view of the link 120 illustrating an elongated solid plate 1102 with two semi circular (rounded) ends. One semicircular end of the link 120 may have bore 1104 while the other semicircular end may have bore 1106. Both the bores 1104, 1106 may be concentric to the respective rounded end. FIG. 11B is a front view of the link 120, which may be configured as a flattened structure with bore 1104 at one end and 1106 at the other end. FIG. 11C is the side view of the link 120 showing a two dimensional view of the link 120 with the respective length and width of the link 120. The bores 1104, 1106 are shown on both sides of the link 120 which may be bored throughout. A fastener (e.g. a pin) (not shown) passing through the bore 1104 on one end of the link 120 may fix the piston 116 (e.g. through the opening 1206 of FIGS. 12A and 12B) whereas the other bore 1106 on the other side may accommodate the actuator 114

(e.g., through the aperture 714 of FIG. 7A through 7C) by the help of another fastener (not shown).

Figure 12C:
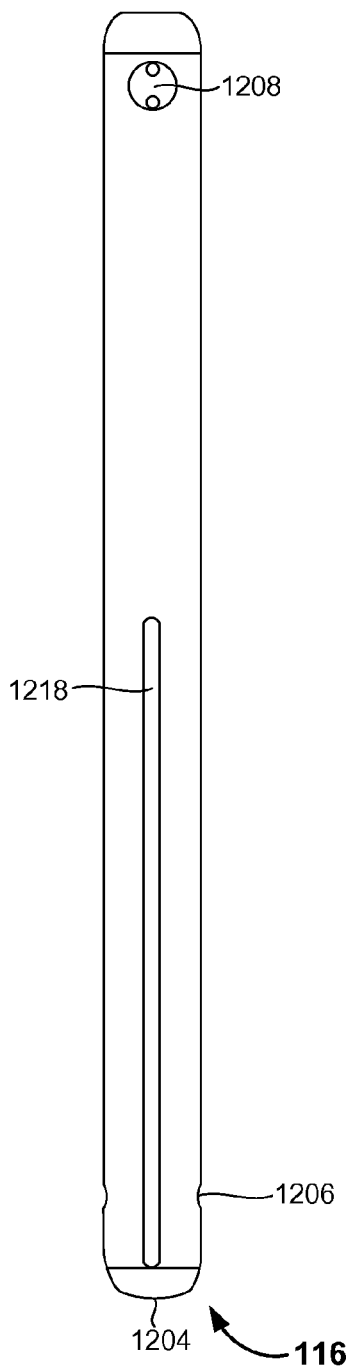
Figure 12A:
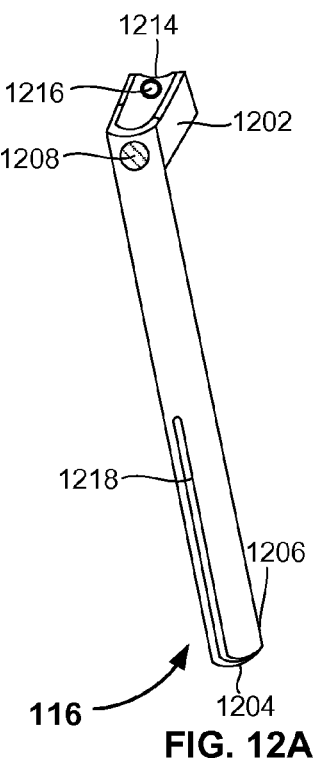

FIGS. 12A through 12E illustrate various views of the piston 116 of the inserter device 100 of FIG. 1 according to an embodiment herein. FIG. 12A is the perspective view illustrating a tubular structure with a dice shaped attachment base 1202 and a free arched head 1204 with an opening 1206 within it. The attachment base 1202 may also include a socket 1208 at its adjacent side. Also there may be a concaved compression 1214 and a circular opening 1216 located at the lower adjacent side of the dice shaped attachment base 1202. An elongated hollow portion 1218 may be present on the upper adjacent side of the piston 116. FIG. 12B is the front view of the piston 116 shown having a tubular shape with the dice shaped attachment base 1202 and the free arched head 1204 with an opening 1206 within it. As shown, the piston 116 may also include two rectangular grooves 1210, 1212 slightly above the attachment base at one adjacent side.

The attachment base 1202 may also include a socket 1208 (shown as a concave furrow) at the other side. FIG. 12C is the right side view showing tube like structure with slightly rounded corners. The upper end may include the hollow 1218 and the base may include the socket 1208. FIG. 12D is the bottom view of the dice shaped attachment base 1202 of piston 116 showing a somewhat 'U' shaped structure having a curved end at one side and a concaved compression 1214 at the other side including the circular opening 1216 near the concaved compression 1214. The opening 1206 may allow a passage of a fastener (e.g., a pin) (not shown) to connect the piston 116 to the link 120 (e.g., as shown in FIG. 5) and the socket 1208 may fix the lock screw 112 to the piston 116. The concaved compression 1214 and the circular opening 1216 may both connect to the shaft 118. The two rectangular grooves 1210 and 1212 may be adapted for the movement of lock lever 106. The hollow portion 1218 allows for the longitudinal movement of the link 120 attached to the actuator 114.

Figure 13C:
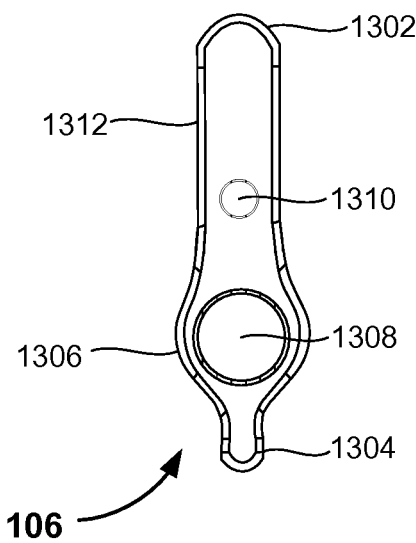
FIGS. 13A through 13D illustrate a perspective view, front view, top view and bottom view respectively of the lock lever of the inserter device of FIG. 1 according to an embodiment herein.
Figure 13B:
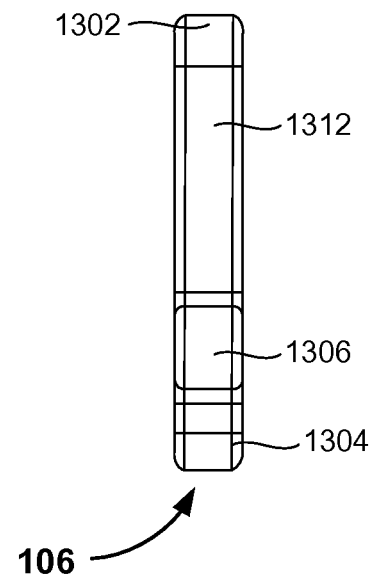
Figure 13D:
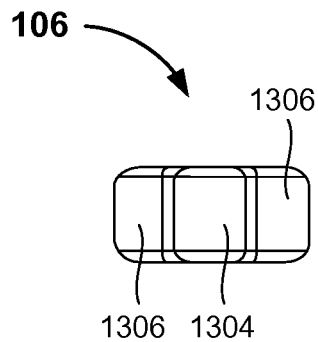
Figure 13A:
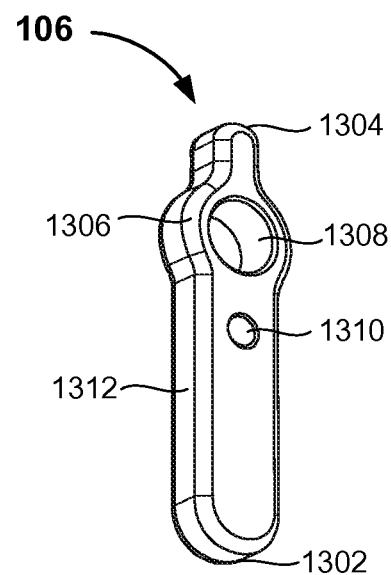

FIGS. 13A through 13D illustrate various views of the lock lever 106 of the inserter device 100 of FIG. 1 according to an embodiment herein. FIG. 13A is a perspective view of the lock lever 106 having an elongated rectangular structure 1312 showing the width. One end 1302 of the lock lever 106 may be semi-circular while the other end 1304 may have a condensed shape. The width of the condensed segment may be smaller as compared to the remaining portion of the lock lever 106. An enlargement forming a groove 1306 which includes a bore 1308 may be present at the condensed end 1304. In addition, the lock lever 106 may include another circular aperture 1310 positioned at a substantially central portion of the lock lever 106. FIG. 13B is the front view of the lock lever 106 having the semi-circular end 1302, the condensed end 1304, the groove 1306 and the elongated rectangular structure 1312. FIG. 13C is the top view of the lock lever 106 illustrating a tubular structure with a semi-circled end 1302, an enlargement groove 1306 with a concentric bore 1308 inside and another condensed end 1304. FIG. 13D is the bottom view having a condensed end 1304 shown as a small rectangular structure, with the groove 1306 shown as slightly curved corners.

The lock lever 106 may be used to lock the position of the piston 116 in at least one position. The condensed end 1304 of the lock lever 106 may fit into the grooves 1210, 1212 of the piston 116 (e.g., as shown in FIG. 5). The groove 1306 may contain a bore 1308, which may be adapted for extending the total length the shaft 118. The semi-circular end 1302 adjacent to the rectangular structure 1312 may be rotated to fix the piston 116 in at least one position. The rotation of the lock lever 106 may lock the piston 116 at a starting position, intermediate position, and final position (e.g., as shown in FIGS. 2 through 4). At the starting position (e.g., FIG. 2) the implant 200 may be in a straight configuration; at the intermediate position (e.g., FIG. 3) the first part 208 of the implant 200 may be curved while at a final position (e.g., FIG. 4) the second part 206 of the implant 200 may be curved.

FIG. 14 illustrates a sectional view of the implant 200 of FIG. 2 connected to the shaft thread 102 of FIG. 1 and the wire 210 of FIG. 2 according to an embodiment herein. The implant 200 may include the first part 204, the second part 206 and the third part 208. The first part 204 may be connected to the second part 206 with a fastener 1402 and the second part is connected to the third part 208 by another fastener 1404. The third part 208 may be connected to the shaft thread 102 at the upper end. The wire 210 may be connected to the third part 208 by a first bolt 1412. The wire 210 may be extended further to be connected to the second part 206 via a first link 1406. Similarly the first link 1406 may be extended further to be connected to the second part 206 via a second link 1408. The second link 1408 may be extended further to connect with the first part 204 via a third link 1410 to be coupled to a rivet 1418, which is positioned perpendicular to the third link 1410. The first link 1406 may be connected to the second link 1408 by a second bolt 1414 and similarly the second link 1408 may be connected to the third link 1410 by a third bolt 1416.

In the starting position (e.g., as shown in FIG. 2) the lock lever 106 may lock the piston 116 (e.g., through the groove 1212 of FIG. 12). The link 1406 may then be prevented from rotation about the axis of the fastener 1404, and the link 1408 may also be prevented from rotation about the axis of the fastener 1402. In the starting position the third part 208 being attached to the shaft thread 102 and the wire 210 (e.g. by the first bolt 1412) may remain aligned to the shaft 118. In the intermediate position (e.g., as shown in FIG. 3) the actuator 114 may be rotated towards the shaft 118 and here the spring 202 may be in a partially compressed state so as to exert a restoring force on the piston 116. When the piston 116 is translated, the wire 210 transmits the action that causes the first part 204 of the implant 200 to rotate about the axis of the fastener 1402 via the third link 1410. In the intermediate position the lock lever 106 may lock the piston 116 (e.g., through the groove 1210 of FIG. 12B). The link 1406 may then be prevented from rotation about the axis of the fastener 1404, and the link 1408 may also be prevented from rotation about the axis of the fastener 1402. Similarly in the final position the spring 202 may be in a state of maximum compression state so as to exert a high restoring force on the piston 116 and when the piston 116 is translated the second part 206 rotates about the axis of the fastener 1404 via the first link 1412.

FIG. 15 illustrates a sectional view of the body 108, the lock screw 112, the piston 116, and the shaft 118 of FIG. 1, the wire 210 of FIGS. 2 through 4, and the opening 816 of FIG. 8 in the inserter device 100 of FIG. 1, according to an embodiment herein. The lock screw 112 may have a handle 1502 and a threaded end 1504. The body 108 may include the piston 116 and the opening 816. The opening 816 may allow a screw (e.g., not shown) which may fix the lock lever 106 into position. The lock screw 112 may pass through the socket 1208 of FIG. 8 (e.g., as shown in FIG. 5) and connect to the wire 210. The lock screw 112 may be rotated by the handle 1502. The rotation of the handle 1502 may be transmitted to the wire 210 by the threaded end 1504. The third part 208 of the implant 200 may then remain aligned to the shaft 118 due to the wire 210.

Figure 16:
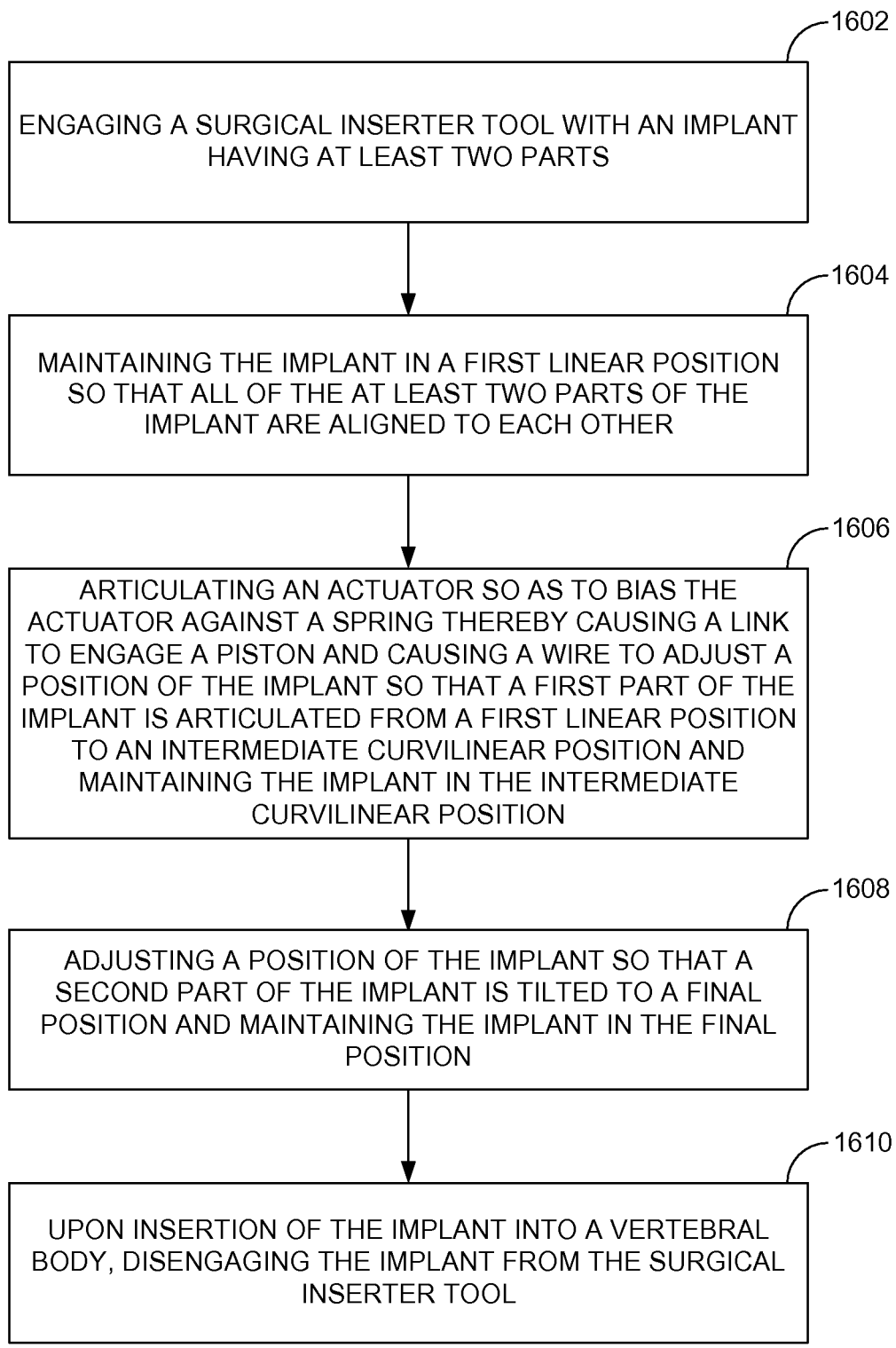
FIG. 16 is a process flowchart that illustrates a method of performing a surgical procedure according to an embodiment herein.

FIG. 16, with reference to FIGS. 1 through 15, is a process flow illustrating a method of performing a surgical procedure according to an embodiment herein, wherein the method comprises: engaging (1402) a surgical inserter tool 100 with an implant 200 having at least two parts 204, 206, 208 that are rotatable with respect to each other; maintaining (1404) the implant 200 in a first linear position so that all of the at least two parts 204-208 of the implant 200 are aligned to each other (e.g. FIG. 2); articulating (1406) an actuator 114 so as to bias the actuator 114 against a spring 202 thereby causing a link 120 to engage a piston 116 and causing a wire 210 to adjust a position of the implant 200 by articulating the implant 200 from a first linear position to an intermediate curvilinear position and maintaining the implant 200 in the intermediate curvilinear position (e.g., FIG. 3); adjusting (1408) a position of the implant 200 so that a second part of the implant 206 is tilted to a final position and maintaining the implant 200 in the final position (e.g., FIG. 4) and upon insertion of the implant 200 into a vertebral body, disengaging (1410) the implant 200 from the surgical inserter 100.

In step 1602, an implant 200 having at least two parts 204, 206, 208 is engaged with (e.g., by an inserter device 100). The implant 200 is engaged to the shaft thread 102 at an end of a shaft 118 that is coupled to a piston 116 which translates the end part 204 of the implant 200 and locking the end part 204 of the implant 200 with a lock screw 112 that is attached to the piston 116 (e.g. as described in FIG. 1). In step 1604, the implant 200 is maintained in a first linear position so that all of at least two parts 204-208 of the implant 200 (e.g. the first part 204, second part 206 and third part 208 of FIG. 2) are aligned to each other. In step 1606, the actuator 114 is articulated so as to bias the actuator 114 against the spring thereby causing the link 120 to engage the piston 116 and causing the wire 210 to adjust a position of the implant 200 so that a first part of the implant 204 is articulated from a first linear position to an intermediate curvilinear position and maintaining the implant 200 in the intermediate curvilinear position (e.g. as shown in the FIG. 3). The position of the implant 200 is adjusted by rotating the actuator 114, which is operatively connected to the wire 210, and the amount of rotation of the actuator 114 determines the position of the implant 200 (e.g. as described in FIG. 1). Here, the implant 200 is maintained in the intermediate curvilinear position by locking the actuator 114 using the lock lever 106 (e.g. as explained in FIG. 3). In step 1608 a position of the implant 200 is adjusted so that a second part 206 of the implant 200 is tilted to a final position and the implant 200 is maintained in a final position (e.g. as illustrated in FIG. 4). The stability of the end part 204 of the implant 200 is increased by absorbing an impact force using a C-shaped ring 104 which surrounds the shaft 118 (e.g. as explained in FIG. 4). In step 1610, upon insertion of the implant 200 into a vertebral body, the implant 200 is disengaged from the surgical inserter tool 100. The disengaging of the implant 200 may be done by rotating the knob 110 that is coupled to the shaft thread 102 through the shaft 118, the shaft thread 102 being connected to the end part 204 of the implant 200 (e.g. as described in FIG. 4).

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A surgical tool for inserting an implant in a vertebral body, the tool comprising:
   a shaft comprising a shaft thread that engages said implant;
   a piston at least a portion of which is traversed by a locking screw coupled to said shaft thread to articulate said implant from a starting linear position to a final curvilinear position;
   an actuator coupled to said piston, wherein said actuator adjusts the position of said implant;
   a wire traversed by said locking screw parallel and exterior to said shaft and positioned between said shaft and said piston, said wire at least partially encircled by said piston at a position where said locking screw traverses the wire and piston; and
   an annular structure surrounding said shaft, wherein said annular structure increases a stability of an end part of said implant upon an impact of insertion,
   wherein said shaft thread and said wire contact said implant at different locations; and wherein actuation of said actuator pulls said wire away from said implant to move said implant from said starting linear position to said final curvilinear position.

2. The tool of claim 1, further comprising a screw attached to said piston that locks said end part of said implant.

3. The tool of claim 1, further comprising a body coupled to the shaft to release said end part of the implant upon rotation of said body.

4. The tool of claim 1, further comprising a lock lever that locks a position of said piston in at least one position.

5. The tool of claim 1, further comprising a knob attached to an end of said shaft and to disengage said implant from said surgical tool upon rotation of said knob.

6. A surgical inserter comprising:
   a body component;
   a non-bendable shaft operatively connected to said body component, wherein said shaft comprises a shaft thread that engages an implant;
   a knob coupled to said shaft;
   an annular structure configured around said shaft;
   an actuator coupled to said body component;
   a link coupled to said actuator;
   a piston positioned parallel to said shaft and coupled to said link;
   a rigid wire comprising an upper end and a lower end coupled to said piston at said upper end, wherein said wire is positioned parallel to said shaft, and wherein said wire is positioned between said shaft and said piston, wherein said rigid wire engages said implant at a different location than said non-bendable shaft;
   a spring operatively coupled to said piston;
   a lock lever coupled to said body component; and
   a lock screw coupled to said piston positioned perpendicular to said piston and said wire; wherein actuation of said actuator pulls said wire away from said implant to move said implant from a starting linear position to a final curvilinear position.

7. The inserter of claim 6, wherein said actuator comprises:
   a plate comprising a plurality of arms positioned at a first end of said plate, wherein said plurality of arms are coupled to said body component;

an aperture positioned at a second end of said plate, wherein said aperture is coupled to said link; and a hollow portion positioned at said second end, wherein said hollow portion allows for movement of said link.

8. The inserter of claim 6, wherein said body component comprises:
   a plurality of openings that allow said shaft and said piston to translate linearly;
   a gap accommodating said lock lever;
   a slot that houses said spring; and
   a hollow portion that allows for movement of said link.

9. The inserter of claim 6, wherein said shaft comprises an attachment head at an end opposite to said shaft thread, and wherein said knob comprises a hollow inner aperture that fixes said attachment head of said shaft.

10. The inserter of claim 7, wherein said link comprises:
    a plate;
    a first semi-circular end; and
    a second semi-circular end,
    wherein said first semi-circular end comprises a bore that couples said link to said piston, and wherein said second semi-circular end comprises a bore that couples said link to said actuator.

11. The inserter of claim 6, wherein said piston comprises:
    a hollow portion positioned at a first end of said piston, wherein said hollow portion allows longitudinal movement of said link;
    a socket positioned at a second end of said piston, wherein said socket fixes said piston to said lock screw, said socket traversing said piston defining access to said wire; and
    at least one groove that accommodates said lock lever.

12. The inserter of claim 6, wherein said lock lever comprises:
    a condensed end positioned at a first end of said lock lever, wherein said condensed end fixes said piston in at least one position;
    a groove adjacent to said condensed end and including a bore to allow for said shaft to translate linearly; and
    a semi-circular end positioned at a second end of said lock lever, wherein said semi-circular end is rotated to fix said piston to said groove.

13. A method of performing a surgical procedure, said method comprising:
    engaging a surgical inserter tool with an implant having at least two parts that are rotatable with respect to each other, wherein said surgical inserter tool comprises:
    a body component;
    a shaft operatively coupled to said body component, wherein said shaft comprises a shaft thread that engages said implant;
    a knob coupled to said shaft;
    an actuator coupled to said body;
    a link coupled to said actuator;
    a piston coupled to said link;
    a wire at least partially encircled by said piston contacting said implant at a position different than said shaft, wherein said wire is parallel to said shaft and positioned between said shaft and said piston; and
    a spring operatively coupled to said piston;
    articulating said actuator so as to bias said actuator against said spring thereby causing said link to engage said piston and causing said shaft thread to adjust a position of said implant so that a first part of said implant is articulated from a first linear position to an intermediate curvilinear position; and
    upon insertion of said implant into a vertebral body, disengaging said implant from said surgical inserter tool;
    wherein actuation of said actuator pulls said wire away from said implant to move said implant from said first linear position to said intermediate curvilinear position.

14. The method of claim 13, further comprising:
    maintaining the implant in the intermediate curvilinear position;
    adjusting a position of the implant so that a second part of the implant is tilted to a final position; and
    maintaining the implant in the final position.

15. The method of claim 14, further comprising maintaining the implant in the first linear position so that all of the at least two parts of the implant are aligned to each other.

16. The method of claim 13, further comprising releasing said implant by rotating said knob.

17. The method of claim 16, further comprising increasing a stability of said implant by absorbing an impact force caused during insertion using a C-shaped ring surrounding said shaft.

18. The method of claim 13, wherein an amount of rotation of said actuator determines the position of said implant.

19. The method of claim 13, wherein said implant is maintained in the intermediate position by locking said actuator in an intermediate position using a lock lever operatively connected to said body and said piston.

20. The method of claim 13, wherein said implant is locked in position with a lock screw that is coupled to said piston.

* * * * *